United States Patent
Kappus et al.

(10) Patent No.: US 10,772,674 B2
(45) Date of Patent: Sep. 15, 2020

(54) DEPLOYMENT MECHANISMS FOR SURGICAL INSTRUMENTS

(71) Applicant: COVIDIEN LP, Mansfield, MA (US)

(72) Inventors: John J. Kappus, Denver, CO (US); David N. Heard, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 1309 days.

(21) Appl. No.: 14/052,871

(22) Filed: Oct. 14, 2013

(65) Prior Publication Data

US 2014/0135763 A1   May 15, 2014

Related U.S. Application Data

(60) Provisional application No. 61/726,980, filed on Nov. 15, 2012.

(51) Int. Cl.
*A61B 18/00* (2006.01)
*A61B 18/14* (2006.01)
(Continued)

(52) U.S. Cl.
CPC .......... *A61B 18/1445* (2013.01); *A61B 17/28* (2013.01); *A61B 17/29* (2013.01); *A61B 18/1442* (2013.01);
(Continued)

(58) Field of Classification Search
CPC ............ A61B 17/29; A61B 2017/2919; A61B 2017/2916; A61B 2017/2936;
(Continued)

(56) References Cited

U.S. PATENT DOCUMENTS 4,005,714 A  2/1977 Hiltebrandt
D249,549 S  9/1978 Pike
(Continued)

FOREIGN PATENT DOCUMENTS

AU  2011253698 A1  12/2011
CN  201299462  9/2009
(Continued)

OTHER PUBLICATIONS

U.S. Appl. No. 08/926,869, James G. Chandler.
(Continued)

*Primary Examiner* — Jaymi E Della
*Assistant Examiner* — Rachel A. Vierra
(74) *Attorney, Agent, or Firm* — Carter, DeLuca & Farrell LLP

(57) ABSTRACT

A surgical instrument includes a first actuation assembly coupled to a first component and movable from a first position to a second position to actuate the first component. A biasing member coupled to the first actuation assembly is configured to bias the first actuation assembly towards the first position. A second actuation assembly is coupled to a second component and is selectively actuatable to actuate the second component. The second actuation assembly is coupled to the first actuation assembly such that actuation of the second actuation assembly effects movement of the first actuating assembly from the first position towards the second position. A linkage assembly is configured to reduce the bias applied to the first actuation assembly when the second actuation assembly effects movement of the first actuation assembly.

15 Claims, 7 Drawing Sheets

(51) Int. Cl.
*A61B 17/29* (2006.01)
*A61B 17/28* (2006.01)

(52) U.S. Cl.
CPC ............. *A61B 2017/2845* (2013.01); *A61B 2017/2912* (2013.01); *A61B 2017/2919* (2013.01); *A61B 2017/2923* (2013.01); *A61B 2017/2932* (2013.01); *A61B 2018/0063* (2013.01); *A61B 2018/00083* (2013.01); *A61B 2018/00601* (2013.01); *A61B 2018/1455* (2013.01)

(58) Field of Classification Search
CPC ........ A61B 18/1442; A61B 2017/2939; A61B 18/1445; A61B 18/1447; A61B 2018/142; A61B 2018/145; A61B 2018/1452; A61B 2018/1455; A61B 2018/1457; A61B 2018/146; A61B 2018/1462; A61B 2018/00833; A61B 2018/00601; A61B 2018/0063; A61B 17/28; A61B 17/2804; A61B 17/2812; A61B 17/282; A61B 17/2833; A61B 17/295; A61B 2017/2808; A61B 2017/2845; A61B 2017/2901; A61B 2017/2903; A61B 2017/2912; A61B 2017/292; A61B 2017/2932
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,026,379 A | 6/1991 | Yoon |
| D343,453 S | 1/1994 | Noda |
| D348,930 S | 7/1994 | Olson |
| D349,341 S | 8/1994 | Lichtman et al. |
| 5,342,359 A | 8/1994 | Rydell |
| D354,564 S | 1/1995 | Medema |
| D358,887 S | 5/1995 | Feinberg |
| 5,611,813 A | 3/1997 | Lichtman |
| D384,413 S | 9/1997 | Zlock et al. |
| H1745 H | 4/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,558,385 B1 | 5/2003 | McClurken et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| 7,208,005 B2 * | 4/2007 | Frecker .................. A61B 17/29 606/167 |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,445,621 B2 | 11/2008 | Dumbauld et al. |
| D582,038 S | 12/2008 | Swoyer et al. |
| 7,481,810 B2 | 1/2009 | Dumbauld et al. |
| 7,628,791 B2 * | 12/2009 | Garrison ............ A61B 18/1445 606/171 |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,771,425 B2 * | 8/2010 | Dycus ................. A61B 18/1445 606/41 |
| 7,789,878 B2 | 9/2010 | Dumbauld et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,342,379 B2 * | 1/2013 | Whitman ......... A61B 17/07207 227/178.1 |
| 8,490,713 B2 * | 7/2013 | Furnish ............. A61B 17/0469 173/18 |
| 8,672,939 B2 * | 3/2014 | Garrison ............ A61B 18/1445 606/51 |
| 8,702,749 B2 * | 4/2014 | Twomey ............ A61B 18/1445 606/205 |
| 9,161,807 B2 * | 10/2015 | Garrison ................ A61B 17/29 |
| 2002/0072766 A1 * | 6/2002 | Hunt ..................... A61B 17/29 606/205 |
| 2005/0113827 A1 * | 5/2005 | Dumbauld ......... A61B 18/1445 606/45 |
| 2006/0129146 A1 | 6/2006 | Dycus et al. |
| 2007/0106297 A1 | 5/2007 | Dumbauld et al. |
| 2009/0012556 A1 | 1/2009 | Boudreaux et al. |
| 2009/0048625 A1 * | 2/2009 | Pedersen ............ A61B 17/2909 606/205 |
| 2009/0112206 A1 | 4/2009 | Dumbauld et al. |
| 2009/0182327 A1 | 7/2009 | Unger |
| 2010/0292690 A1 | 11/2010 | Livneh |
| 2011/0087218 A1 * | 4/2011 | Boudreaux ........ A61B 18/1445 606/41 |
| 2011/0319889 A1 | 12/2011 | Chojin et al. |
| 2012/0083827 A1 | 4/2012 | Artale et al. |
| 2012/0209263 A1 | 8/2012 | Sharp et al. |
| 2013/0218198 A1 | 8/2013 | Larson et al. |
| 2014/0025052 A1 * | 1/2014 | Nau, Jr. ............. A61B 18/1445 606/13 |
| 2016/0106496 A1 * | 4/2016 | Artale ................. A61B 17/285 606/42 |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |

(56) References Cited

FOREIGN PATENT DOCUMENTS

| | | |
|---|---|---|
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 A1 | 5/2005 |
| EP | 1769765 A1 | 4/2007 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A3 | 9/2002 |
| WO | 06/021269 A1 | 3/2006 |
| WO | 05110264 A3 | 4/2006 |
| WO | 2007118/608 A1 | 10/2007 |
| WO | 08/040483 A1 | 4/2008 |
| WO | 20111018154 A1 | 2/2011 |

OTHER PUBLICATIONS

U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremeich.
U.S. Appl. No. 13/421,373, John R. Twomey.
U.S. Appl. No. 13/430,325, William H. Nau, Jr.
U.S. Appl. No. 13/433,924, Keir Hart.
U.S. Appl. No. 13/448,577, David M. Garrison.
U.S. Appl. No. 13/460,455, Luke Waaler.
U.S. Appl. No. 13/461,335, James D. Allen, IV.
U.S. Appl. No. 13/461,378, James D. Allen, IV.
U.S. Appl. No. 13/461,397, James R. Unger.
U.S. Appl. No. 13/461,410, James R. Twomey.
U.S. Appl. No. 13/466,274, Stephen M. Kendrick.
U.S. Appl. No. 13/467,767, Duane E. Kerr.
U.S. Appl. No. 13/470,775, James D. Allen, IV.
U.S. Appl. No. 13/482,589, Eric R. Larson.
U.S. Appl. No. 13/483,733, Dennis W. Butcher.
U.S. Appl. No. 13/537,517, David N. Heard.
U.S. Appl. No. 13/537,577, Tony Moua.
U.S. Appl. No. 13/708,335, Dumbauld.
U.S. Appl. No. 13/731,674, Siebrecht.
U.S. Appl. No. 13/799,173, Larson.
U.S. Appl. No. 13/803,636, Kerr.
U.S. Appl. No. 13/803,762, Kerr.
U.S. Appl. No. 13/803,884, Kerr.
U.S. Appl. No. 13/804,010, Kerr.
U.S. Appl. No. 13/833,823, Garrison.
U.S. Appl. No. 13/834,703, Garrison.
U.S. Appl. No. 13/835,004, Twomey.
U.S. Appl. No. 13/838,945, Stoddard.
U.S. Appl. No. 13/868,732, Mueller.
U.S. Appl. No. 13/893,527, Horner.
U.S. Appl. No. 13/903,091, Nau.
U.S. Appl. No. 13/903,116, Nau.
U.S. Appl. No. 13/903,223, Payne.
U.S. Appl. No. 13/909,362, Kerr.
U.S. Appl. No. 13/911,674, Kerr.
U.S. Appl. No. 13/920,643, Nau.
U.S. Appl. No. 13/922,377, Allen.
U.S. Appl. No. 13/922,975, McKenna.
U.S. Appl. No. 13/933,409, Mueller.
U.S. Appl. No. 13/933,683, Nau.
U.S. Appl. No. 13/936,510, Kerr.
U.S. Appl. No. 13/947,991, Kerr.
U.S. Appl. No. 13/969,204, Bucciaglia.
U.S. Appl. No. 13/969,278, Kerr.
U.S. Appl. No. 14/017,572, Arya.
U.S. Appl. No. 14/019,031, Garrison.
U.S. Appl. No. 14/019,094, Garrison.
Michael Choti, "Abdominoperineal Resection with the LigaSure Vessel Sealing System and LigaSure Atlas 20 cm Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

(56) References Cited

OTHER PUBLICATIONS

Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
European Search Report EP13174297 dated Nov. 7, 2013.
International Search Report PCT/US2013/065659 dated Jan. 8, 2014.
Extended European Search Report issued in corresponding application No. 13855800.2 dated Jul. 11, 2016.

* cited by examiner

DEPLOYMENT MECHANISMS FOR SURGICAL INSTRUMENTS

CROSS REFERENCE TO RELATED APPLICATION

The present application claims the benefit of and priority to U.S. Provisional Application Ser. No. 61/726,980, filed on Nov. 15, 2012, the entire contents of which are incorporated herein by reference.

BACKGROUND

Technical Field

The present disclosure relates to surgical instruments and, more particularly, to deployment mechanisms for deploying, e.g., actuating, one or more components of a surgical instrument.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween.

As can be appreciated, as additional functional components are added to the surgical instrument, additional deployment structures or deployment structures capable of actuating more than one component are required. However, multiple deployment structures and/or combined deployment structures may be limited by spatial constraints within the housing of the surgical instrument and/or functional constraints of the components, e.g., where a combined deployment structure imparts additional force requirements for deploying one or more of the components coupled thereto.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a surgical instrument is provided including an end effector assembly, a knife, a trigger assembly, a biasing member, a monopolar assembly, a lever assembly, and a linkage. The end effector assembly includes first and second jaw members. One or both of the jaw members is movable relative to the other between a spaced-apart position and an approximated position for grasping tissue therebetween. The knife is selectively movable relative to the jaw members between a retracted position and an extended position, wherein the knife extends between the jaw members to cut tissue grasped therebetween. The trigger assembly is coupled to the knife and is selectively movable from an un-actuated position to an actuated position to move the knife from the retracted position to the extended position. The biasing member is coupled to the trigger assembly and is configured to apply a biasing force to the trigger assembly to bias the trigger assembly towards the un-actuated position. The monopolar assembly includes an energizable member and is selectively movable relative to the jaw members between a stored position and a use position, wherein the energizable member extends distally from the jaw members. The lever assembly is coupled to the monopolar assembly and is selectively movable from a first position to a second position to move the monopolar assembly from the stored position to the use position. The lever assembly is also coupled to the trigger assembly such that movement of the lever assembly from the first position to the second position effects movement of the trigger assembly from the un-actuated position towards the actuated position. The linkage assembly is coupled to the lever assembly and the biasing member and is configured to reduce the biasing force applied to the trigger assembly when the lever assembly effects movement of the trigger assembly from the un-actuated position towards the actuated position.

In one aspect, the monopolar assembly further includes an insulative sleeve. Upon movement of the monopolar assembly from the stored position to the use position, the insulative sleeve is moved from a proximal position to a distal position, wherein the insulative sleeve is disposed about the jaw members.

In another aspect, the lever assembly is configured to contact the trigger assembly upon actuation of the lever assembly to urge the trigger assembly from the un-actuated position towards the actuated position.

In yet another aspect, the trigger assembly and lever assembly are partially (or entirely) disposed within a housing configured to guide movement of the trigger assembly and/or lever assembly.

A surgical instrument provided in accordance with the present disclosure includes a first actuation assembly, a biasing member, a second actuation assembly, and a linkage assembly. The first actuation assembly is coupled to a first component and is selectively movable from a first position to a second position to actuate the first component. The biasing member is coupled to the first actuation assembly and is configured to apply a biasing force to the first actuation assembly to bias the first actuation assembly towards the first position. The second actuation assembly is coupled to a second component and is selectively actuatable to actuate the second component. The second actuation assembly is also coupled to the first actuation assembly such that actuation of the second actuation assembly effects movement of the first actuating assembly from the first position towards the second position. The linkage assembly is coupled to the second actuation assembly and the biasing member. The linkage assembly is configured to reduce the biasing force applied to the first actuation assembly when the second actuation assembly effects movement of the first actuation assembly from the first position towards the second position.

In one aspect, a portion of the second actuation assembly is configured to contact a portion of the first actuation assembly upon actuation of the second actuation assembly to urge the first actuation assembly from the first position towards the second position.

In another aspect, the first actuation assembly includes a trigger pivotable from an un-actuated position to an actuated position for moving the first actuation assembly from the first position to the second position.

In another aspect, the second actuation assembly includes a lever pivotable from a proximal position to a distal position for actuating the second actuation assembly.

In yet another aspect, the first and second actuation assemblies are at least partially disposed within a housing.

In still yet another aspect, the housing defines at least one track configured to guide movement of at least one of the first actuation assembly between the first and second positions and actuation of the second actuation assembly.

In another aspect, the biasing member is coupled to the first actuation assembly at a first end thereof and to the linkage assembly at a second end thereof.

In yet another aspect, the first actuation assembly is configured to move the first end of the biasing member distally upon movement of the first actuation assembly from the first position towards the second position.

In still another aspect, the linkage is configured to maintain the second end of the biasing member in substantially fixed position when the second actuation assembly is un-actuated.

In still yet another aspect, the linkage is configured to move the second end of the biasing member distally upon actuation of the second actuation assembly.

In another aspect, the linkage is configured to move the second end of the biasing member distally a distance that is substantially equal to a distance the first actuation assembly is configured to move the first end of the biasing member distally upon movement of the first actuation assembly from the first position towards the second position.

A method of actuating components of a surgical instrument is also provided in accordance with the present disclosure. The method includes moving a first actuation assembly against a biasing force from a first position to a second position to actuate a first component, returning the first actuation assembly from the second position back to the first position, and moving a second actuation assembly to actuate a second component. Moving the second actuation assembly effects movement of the first actuation assembly from the first position to the second position under a reduced biasing force.

In one aspect, a trigger is moved from an un-actuated position to an actuated position to move the first actuation assembly from the first position to the second position.

In another aspect, a lever is moved from a proximal position to a distal position to move the second actuation assembly.

In another aspect, a biasing member applies the biasing force to bias the first actuation assembly towards the first position.

In still another aspect, the first actuation assembly is returned from the second position to the first position under the biasing force.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
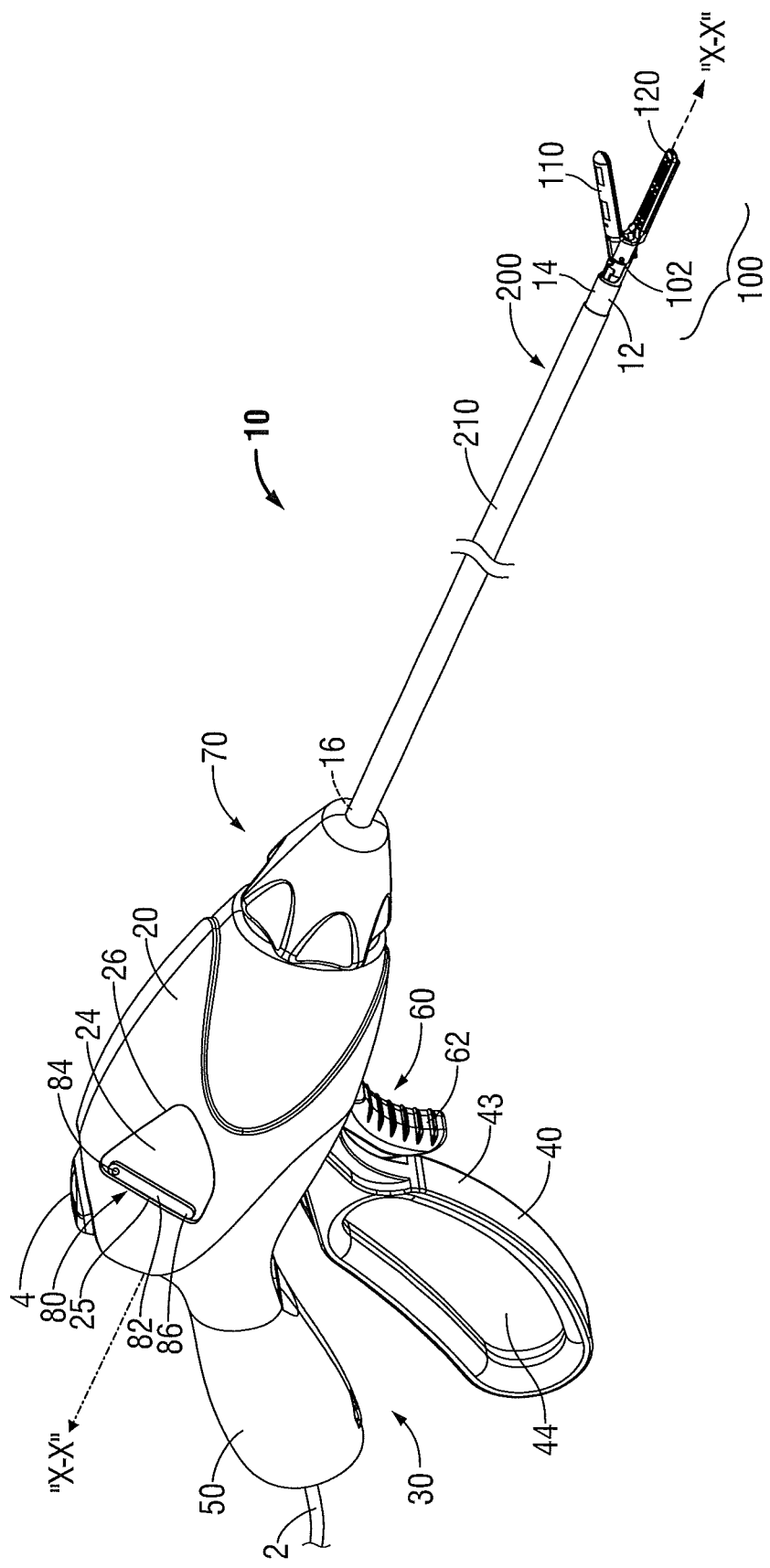
FIG. 1 is a front, perspective view of an endoscopic surgical forceps configured for use in accordance with the present disclosure.

Referring now to FIGS. 1-7, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for actuating, moving, and/or deploying the assemblies and/or components of the surgical instrument. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIGS. 1-7, forceps 10 defines a longitudinal axis "X-X" and includes a housing 20, a handle assembly 30, a trigger assembly 60, a rotating assembly 70, a lever assembly 80, an end effector assembly 100, and a monopolar assembly 200. Forceps 10 further includes a shaft 12 having a distal end 14 configured to mechanically engage end effector assembly 100 and a proximal end 16 that mechanically engages housing 20. Forceps 10 also includes electrosurgical cable 2 that connects forceps 10 to a generator (not shown) or other suitable power source, although forceps 10 may alternatively be configured as a battery powered instrument. Cable 2 includes wires 2a extending therethrough that have sufficient length to extend through shaft 12 in order to provide electrical energy to at least one of the electrically-conductive plates 112, 122 of jaw members 110, 120, respectively, of end effector assembly 100, e.g., upon activation of activation switch 4 in a bipolar mode. Wires 2b of cable 2, on the other hand, extend through housing 20 in order to provide electrical energy to monopolar assembly 200, e.g., upon activation of activation switch 4 in a monopolar mode. Rotating assembly 70 is rotatable in either direction about longitudinal axis "X-X" to rotate end effector 100 and monopolar assembly 200 about longitudinal axis "X-X." Housing 20 houses the internal working components of forceps 10, which will be described in detail, in turn, below.

Figure 2:
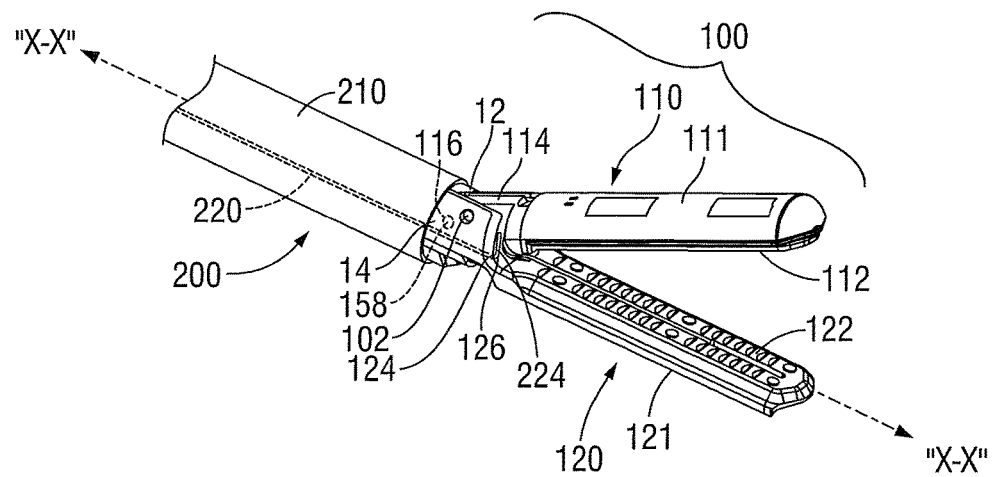
FIG. 2 is an enlarged, front, perspective view of an end effector assembly of the forceps of FIG. 1, wherein jaw members of the end effector assembly are disposed in a spaced-apart position and wherein a monopolar assembly is disposed in a retracted position.
Figure 3:
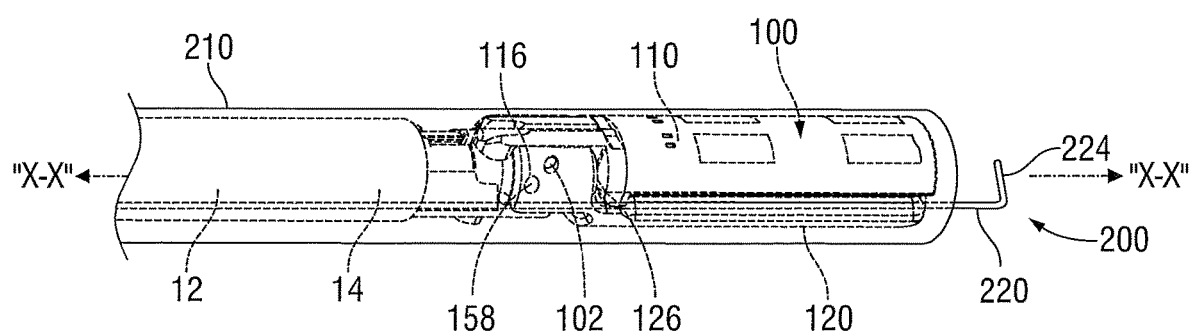
FIG. 3 is an enlarged, rear, perspective view of the end effector assembly of FIG. 2, wherein the jaw members are disposed in an approximated position and wherein the monopolar assembly is disposed in a deployed position.

Referring to FIGS. 1-3, end effector assembly 100 is shown attached at a distal end 14 of shaft 12 and includes a pair of opposing jaw members 110, 120 pivotably coupled to one another about a pivot 102. Each of the jaw members 110 and 120 includes an electrically-insulative outer jaw housing 111, 121 an electrically-conductive plate 112, 122 disposed atop respective jaw housings 111, 121, and a proximally-extending flange 114, 124, respectively. Pivot 102 extends through flanges 114, 124 to pivotably couple jaw members 110, 120 to one another. One or both of plates 112, 122 are adapted to connect to a source of energy (not explicitly shown), e.g., via wires 2a (FIG. 4), for conducting energy therebetween and through tissue grasped between jaw members 110, 120 to treat, e.g., seal, tissue. More specifically, in some embodiments, end effector assembly 100 defines a bipolar configuration wherein plate 112 is charged to a first electrical potential and plate 122 is charged to a second, different electrical potential such that an electrical potential gradient is created for conducting energy between plates 112, 122 and through tissue grasped therebetween for treating e.g., sealing, tissue. Activation switch 4 (FIG. 1) is coupled to wires 2a (FIG. 4), thus allowing the user to selectively apply energy to plates 112, 122 of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In one some embodiments, a knife channel 115, 125 (FIGS. 8A-8D) may be defined within one or both of jaw members 110, 120 to permit reciprocation of knife 184 therethrough, e.g., upon actuation of trigger 62 of trigger assembly 60.

Figure 4:
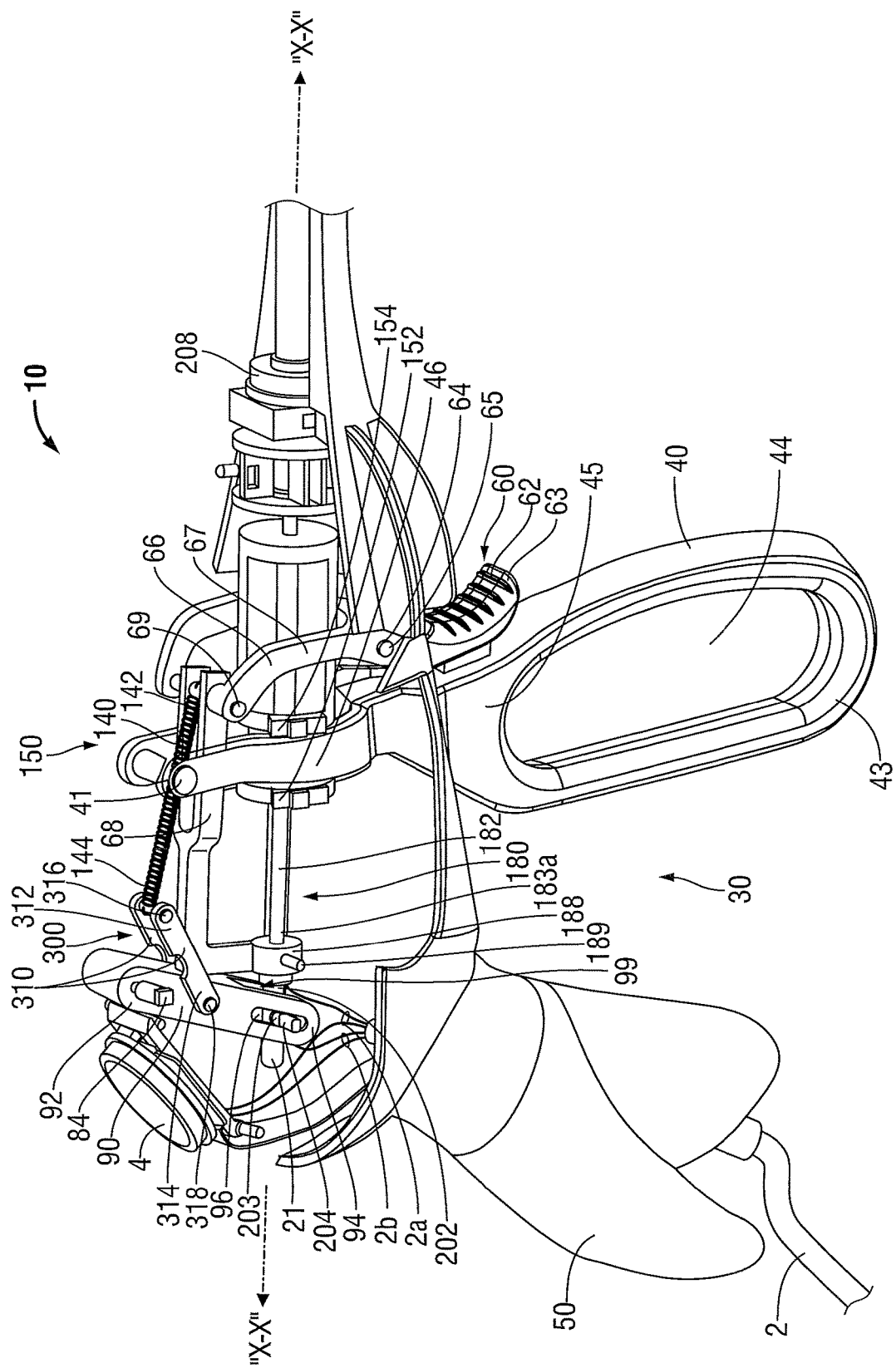
FIG. 4 is a side, perspective, cut-away view of the housing of the forceps of FIG. 1 showing the internal components disposed within the housing.
Figure 5:
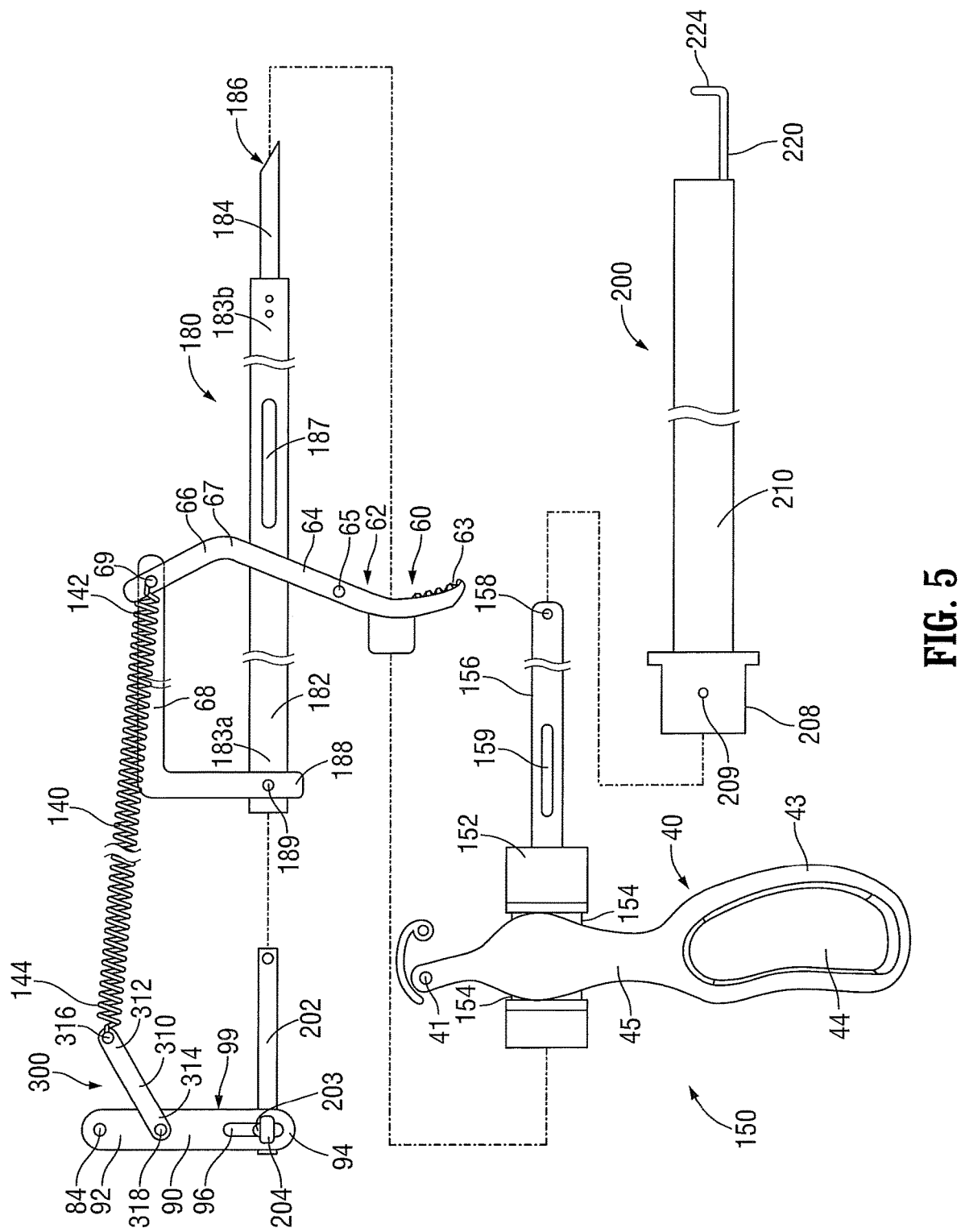
FIG. 5 is an exploded, side view of the internal working components of the forceps of FIG. 1.

With reference to FIGS. 1, 4, and 5, handle assembly 30 includes a movable handle 40 and a fixed handle 50. Fixed handle 50 is integrally associated with housing 20 and movable handle 40 is movable relative to fixed handle 50. Movable handle 40 is pivotably coupled to housing 20 via pivot 41 and is pivotable about pivot 41 and relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position. Movable handle 40 is ultimately connected to a drive assembly 150 that, together, mechanically cooperate to impart movement of jaw members 110, 120 between a spaced-apart position (FIG. 8A) and an approximated position (FIG. 8B) to grasp tissue between electrically-conductive plates 112, 122 of jaw members 110, 120, respectively. Drive assembly 150 will be described in greater detail below.

Continuing with reference to FIGS. 1, 4, and 5, as mentioned above, drive assembly 150 interconnects movable handle 40 and end effector assembly 100. Movable handle 40 includes a handle portion 43 defining a finger hole 44 and a bifurcated arm 45 extending upwardly from handle portion 43 and into housing 20. Arm 45 is bifurcated to define first and second spaced-apart flanges 46 that are pivotably coupled to housing 20 at the free ends thereof via pivot 41. Flanges 46 extend on either side of drive assembly 150 and are coupled thereto to facilitate movement of jaw members 110, 120 between the spaced-apart position and approximated positions. More specifically, flanges 46 extend upwardly on either side of mandrel 152 and are disposed within lateral slots 154 defined within mandrel 152 such that pivoting of movable handle 40 about pivot 41 between the initial and compressed positions effects corresponding longitudinal translation of mandrel 152.

Mandrel 152 is fixedly engaged about the proximal end of an elongated drive member 156. Elongated drive member 156 extends distally from housing 20 and through shaft 12, ultimately coupling to end effector assembly 100. More specifically, elongated drive member 156 includes a transverse drive pin 158 disposed towards a distal end thereof that is pivotably disposed within aperture 116 defined within proximal flange 114 of movable jaw member 110, such that proximal translation of elongated drive member 156 pulls jaw member 110 to pivot relative to jaw member 120 towards the approximated position, while distal translation of elongated drive member 156 pushes jaw member 110 to pivot relative to jaw member 120 towards the spaced-apart position. As such, pivoting of movable handle 40 between the initial and compressed positions effects movement of drive member 156 (between a first, un-actuated position and a second, actuated position), to pivot jaw members 110, 120 between the spaced-apart and approximated positions.

Trigger assembly 60, as shown in FIGS. 1 and 4-6, is coupled to knife assembly 180 such that trigger 62 is selectively actuatable from a first, un-actuated, distal position to a second, actuated, proximal position to advance knife 184 from a retracted position (FIG. 8B), wherein knife 184 is disposed proximally of jaw members 110, 120, to an extended position, wherein knife 184 extends between jaw members 110, 120 and through knife channels 115, 125, respectively (FIG. 8C), to cut tissue grasped between jaw members 110, 120. Trigger assembly 60 will be described in greater detail below. Knife assembly 180 includes a knife drive rod 182 defining proximal and distal ends 183a, 183b, respectively. Proximal end 183a of knife drive rod 182 is coupled to connector 68 of trigger assembly 60 by a base member 188 that defines a pair of opposed, lateral protrusions 189. Knife drive rod 182 extends distally through elongated drive member 156, which extends through mandrel 152 and shaft 12, ultimately engaging the proximal end of knife 184. Knife 184 defines a distal cutting edge 186 configured to facilitate the cutting of tissue upon translation of knife 184 therethrough.

Trigger assembly 60 includes a trigger 62 having a toggle member 63 and a bifurcated arm 66 extending upwardly from toggle member 63 and into housing 20. Trigger 62 is pivotably coupled to housing 20 via pivot 65, which extends through an intermediate portion 64 of trigger 62. Arm 66 is bifurcated to define first and second spaced-apart flanges 67 to permit passage of arm 66 about drive assembly 150. A pin 69 pivotably couples flanges 67 of trigger 62 to connector 68. Connector 68 extends proximally through housing 20, ultimately coupling to the proximal end of knife drive rod 182 of knife assembly 180. Accordingly, upon pivoting of trigger 62 about pivot pin 65 and relative to housing 20 from the un-actuated position towards the actuated position, flanges 67 are rotated to pull connector 68 distally such that knife drive rod 182 is pushed distally (from a first, un-actuated position to a second, actuated position) to translate knife 184 from the retracted position towards the extended position. On the other hand, upon return of trigger 62 towards the un-actuated position, flanges 67 are rotated to push connector 68 proximally such that knife drive rod 182 is pulled proximally (from the second, actuated position back to the first, un-actuated position) to translate knife 184 back towards the retracted position. A biasing member 140, e.g., a coil spring, is coupled to pin 69 at a distal end 142 thereof and to a linkage assembly 300, which will be described in greater detail below, at a proximal end 144 thereof for biasing trigger 62 towards the un-actuated position, thereby biasing knife 184 towards the retracted position. Further, with additional reference to FIG. 7, housing 20 may define a pair of longitudinal tracks 21 on opposing sides thereof (only one is shown) that are configured to receive opposed, lateral protrusions 189 of base member 188 of knife drive rod 182 to guide translation of knife drive rod 182 and, thus, knife 184 between the retracted and extended positions.

Referring to FIGS. 1 and 4-6, lever assembly 80 is shown. Although lever assembly 80 is shown disposed on only one side of housing 20, lever assembly 80 may be configured to define a symmetrical configuration having substantially similar components disposed on either side of housing 20, thus allowing actuation of lever assembly 80 from either side of housing 20. However, for purposes of simplicity, only one side of lever assembly 80 will be described herein.

Lever assembly 80 is disposed within a recess 24 defined on an exterior side surface of housing 20 (although lever assembly 80 may also be positioned at any other suitable location) and includes a lever 82 that is rotatable about a pivot 84 between a proximal position, wherein free end 86 of lever 82 is disposed at a proximal end 25 of recess 24, and a distal position, wherein free end 86 of lever 82 is disposed at a distal end 26 of recess 24. In configurations where lever assembly 80 defines a symmetrical configuration, a pair of levers 82 are provided on either side of housing 20, each of which is coupled to one end of pivot 84. Pivot 84 is rotatably coupled to housing 20 and extends through housing 20. A pair of arms 90 disposed within housing 20 on opposed sides thereof are coupled to pivot 84 and extend therefrom. More specifically, each arm 90 is engaged about pivot 84 of lever assembly 80 at the first end 92 thereof such that rotation of pivot 84 relative to housing 20, e.g., via rotation of lever 82, effects rotation of second ends 94 of arms 90 about first ends 92 thereof. Each arm 90 further includes a slot 96 defined therethrough towards second end 94 thereof. Slots 96 are configured to slidably receive transverse pin 204 of hub 203 of drive shaft 202 of monopolar assembly 200 therein such that, upon rotation of arms 90 about pivot 84, e.g., upon actuation of lever 82, the angular displacement of arms 90 is converted into longitudinal translation of hub 203 and, thus, longitudinal translation of drive shaft 202 of monopolar assembly 200 (from a first, un-actuated position, to a second, actuated position) to move insulative sleeve 210 and energizable rod member 220 of monopolar assembly 200 from the retracted position (FIGS. 2 and 8C) to the deployed position (FIGS. 3 and 8D), as will be described in greater detail below.

With reference to FIGS. 1-7, monopolar assembly 200 includes a drive shaft 202, a ferrule 208, an insulative sleeve 210, and an energizable rod member 220. Drive shaft 202 includes a hub 203 disposed at the proximal end thereof. Hub 203 includes a having a transverse pin 204 extending outwardly therefrom. Transverse pin 204, as mentioned above, is configured for slidable receipt within slots 96 of arms 90 of lever assembly 80 such that pivotal movement of lever 82 effects longitudinal translation of transverse pin 204 and, thus, drive shaft 202. Opposed ends of transverse pin 204 are configured for slidable receipt within longitudinal tracks 21 of housing 20 (see FIG. 7) to guide longitudinal translation of drive shaft 202 and, thus, monopolar assembly 200 between the retracted position (FIGS. 2 and 8C) and the deployed position (FIGS. 3 and 8D).

Drive shaft 202 is slidably disposed within knife drive rod 182 and elongated drive member 156 and is coupled to ferrule 208 towards the distal end thereof. More specifically, knife drive rod 182 and elongated drive member 156 each define a longitudinal slot 187, 159, respectively, therethrough, that allows engagement of ferrule 208, which is disposed about shaft 12, to drive shaft 202 of monopolar assembly 200 via one or more pins 209, although other suitable engagements may also be provided. Ferrule 208 engages insulative sleeve 210 and energizable rod member 220 to drive shaft 202 such that longitudinal translation of drive shaft 202 effects corresponding longitudinal translation of insulative sleeve 210 and energizable rod member 220. Accordingly, actuation of lever 82 may be effected to translate drive shaft 202 distally, thereby moving insulative sleeve 210 and energizable rod member 220 from the retracted position (FIGS. 2 and 8C) to the deployed position (FIGS. 3 and 8D).

Insulative sleeve 210 is slidably disposed about shaft 12 and is configured for translation about and relative to shaft 12 between a retracted position (FIGS. 2 and 8C), where insulative sleeve 210 is disposed proximally of end effector assembly 100, and a deployed position (FIGS. 3 and 8D), wherein insulative sleeve 210 is substantially disposed about end effector 100 so as to electrically insulate plates 112, 122 of jaw members 110, 120, respectively, from the surroundings of insulative sleeve 210. Energizable rod member 220 extends through sleeve 210 and distally therefrom, ultimately defining an electrically-conductive distal tip 224. Distal tip 224 may be hook-shaped (as shown), or may define any other suitable configuration, e.g., linear, circular, angled, etc. Energizable rod member 220 and, more specifically, distal tip 224 thereof, functions as the active electrode of monopolar assembly 200. Sleeve 210 and rod member 220 may be fixedly engaged to one another and/or ferrule 208 such that sleeve 210 and rod member 220 move in concert with one another between their retracted position (FIGS. 2 and 8C) and the deployed position (FIG. 8D), e.g., upon actuation of lever 82 (FIG. 1), although other configurations may also be provided. Wires 2b, which extend from electrosurgical cable 2 through housing 20, are coupled to energizable rod member 220 to provide energy to energizable rod member 220, e.g., upon actuation of activation switch 4 (FIG. 1) in a monopolar mode, for treating tissue in a monopolar mode of operation.

Figure 8A:
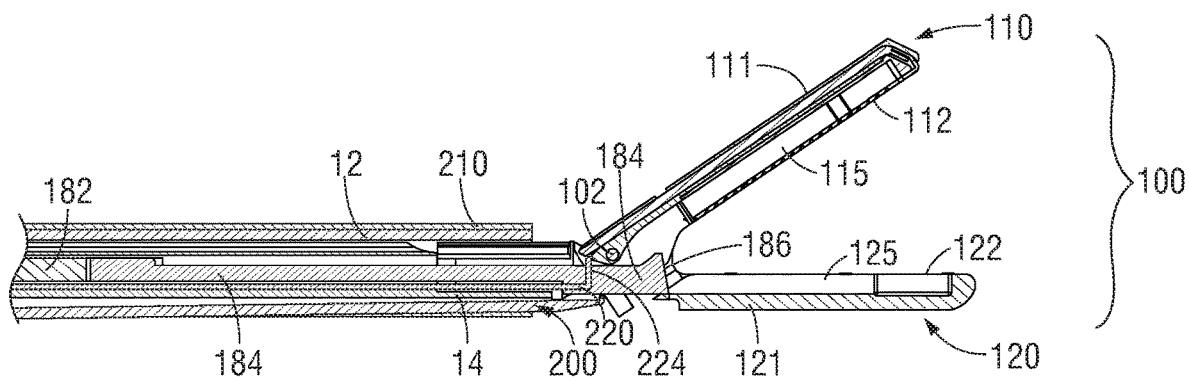
FIG. 8A is a longitudinal, cross-sectional view of the end effector assembly of FIG. 2 with the jaw members disposed in a spaced-apart position.
Figure 8B:
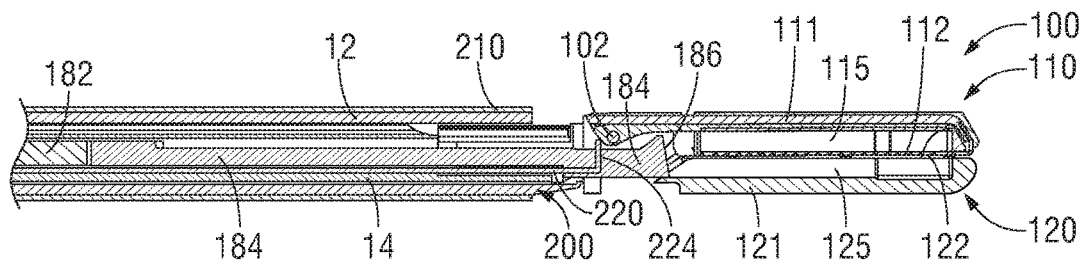
FIG. 8B is a longitudinal, cross-sectional view of the end effector assembly of FIG. 2 with the jaw members disposed in an approximated position.
Figure 8C:
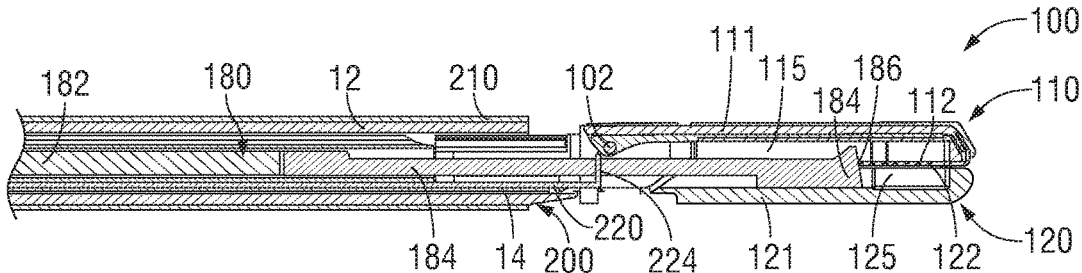
FIG. 8C is a longitudinal, cross-sectional view of the end effector assembly of FIG. 2 with the jaw members disposed in the approximated position and a knife disposed in an extended position.

In the retracted position, as shown in FIGS. 2 and 8C, distal tip 224 of monopolar assembly 200 is disposed within an insulating member 126, e.g., an insulated recess defined within proximal flange 124 of jaw member 120, although other configurations are also contemplated. Insulating member 126 is electrically-insulated such that distal tip 224 of rod member 220 is isolated from electrically-conductive plates 112, 122 of jaw members 110, 120, respectively, and from surrounding tissue when disposed in the retracted position. Alternatively, distal tip 224 of rod member 220 may only be insulated from plate 112. In such configurations, distal tip 224 of rod member 220 is capable of being energized to the same polarity as plate 122. In the extended position, as shown in FIGS. 3 and 8D, distal tip 224 of rod member 220 extends distally from end effector assembly 100 and insulative sleeve 210, which substantially surrounds end effector assembly 100. In this position, energy may be applied to distal tip 224 of rod member 220 to treat tissue, e.g., via activation of activation switch 4 (FIG. 1) in the monopolar mode.

Figure 6:
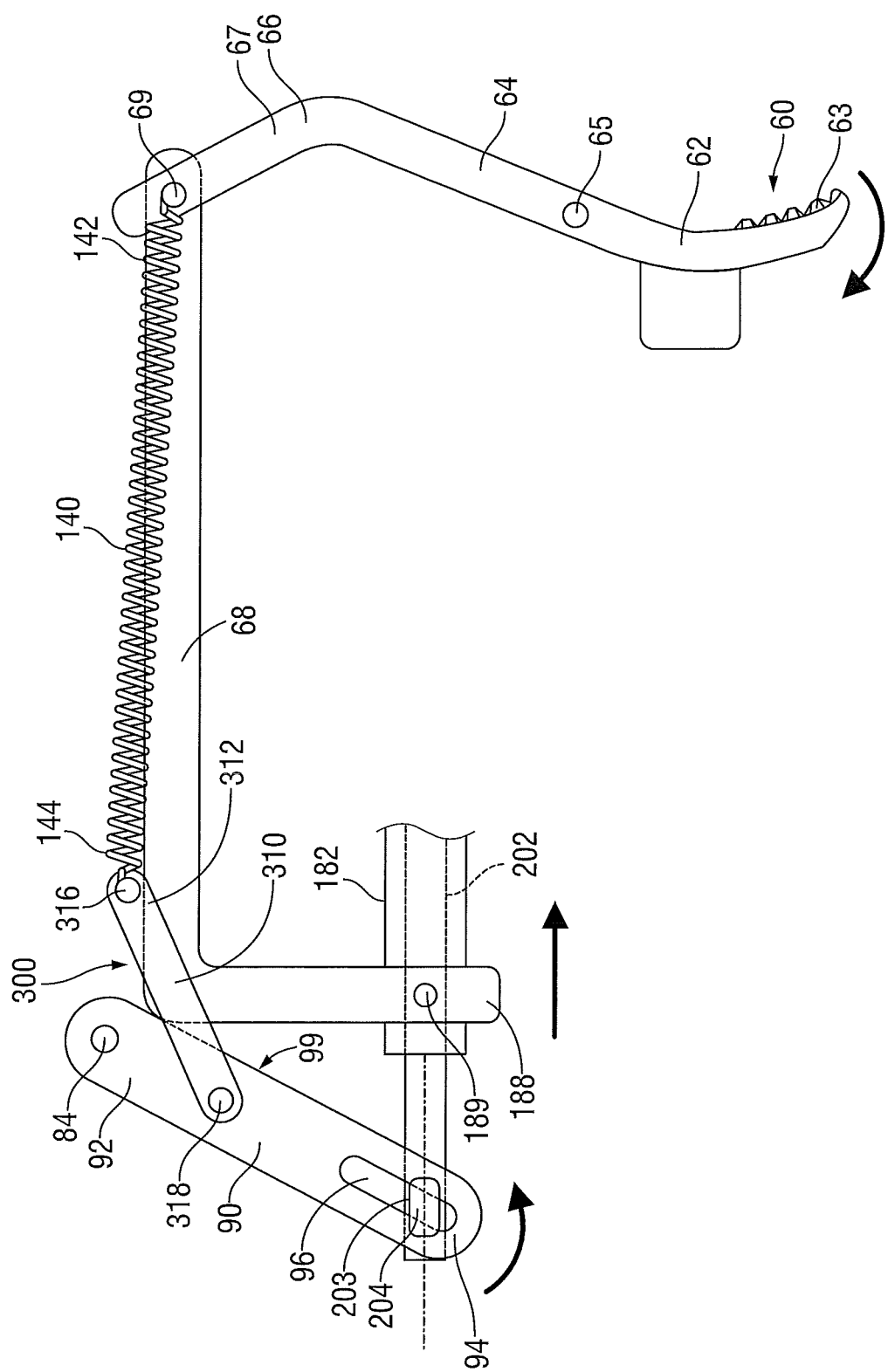
FIG. 6 is an exploded, side view of the lever assembly and trigger assembly of the forceps of FIG. 1.

With reference to FIGS. 4 and 6, in conjunction with FIGS. 1-3, 5, and 7, a portion of distal surfaces 99 of arms 90 abut the proximal end of connector 68 of trigger assembly 60 when trigger 62 is disposed in the un-actuated position, e.g., when knife 184 is disposed in the retracted position. As such, upon actuation of lever 82 to rotate arms 90 about pivot 84 in the distal direction to thereby translate monopolar assembly 200 to the deployed position, distal surfaces 99 of arms 90 urge connector 68 distally. Distal urging of connector 68, as mentioned above, translates knife 184 from the retracted position towards the extended position. This configuration, wherein arms 90 abut connector 68 such that knife 184 is translated to the extended position upon movement of monopolar assembly 200 to the deployed position is advantageous in that it allows these components to assume a more compact configuration, freeing up space within housing 20 for other components and/or allowing for a more compact housing 20 to be used. However, urging connector 68 distally to translate knife 184 from the retracted position towards the extended position upon deployment of monopolar assembly 200 requires that lever 82 be actuated with sufficient force so as to overcome the biasing force of biasing member 140, which, as described above, biases trigger assembly 60 and, thus, connector 68 proximally.

In order to reduce the force required to actuate lever 82 while still providing the space-conserving benefits described above, a linkage assembly 300 is operably coupled between biasing member 140 of trigger assembly 60 and arms 90 of lever assembly 80. However, the presently disclosed linkage assembly 300 is not limited to this particular use, as linkage assembly 300 may alternatively be used with any suitable components and/or assemblies of a surgical instrument.

Linkage assembly 300 includes a pair of spaced-apart linkage members 310, each of which defines a first end 312 and a second end 314. A first pin 316 extends between and outwardly from linkage members 310 at the first ends 312 thereof. Proximal end 144 of biasing member 140 is coupled to the portion of first pin 316 that extends between linkage members 310, while the outwardly-extending portions of first pin 316 are configured for slidable receipt within linkage tracks 27 defined within housing 20, as will be described in greater detail below. A second pin 318 extends between linkage members 310 at the second ends 314 thereof for pivotably coupling linkage members 310 to arms 90 of lever assembly 80. As such, and as will be described in greater detail below, although the distal advancement of connector 68, which is effected by actuation of lever 82 to translate monopolar assembly 200 to the deployed position, pulls distal end 142 of biasing member 140 distally, actuation of lever 82 also moves linkage members 310 and, thus, proximal end 144 of biasing member 140 distally, such that the tension on biasing member 140 is reduced (or removed) and a reduced biasing force (or no biasing force) from biasing member 140 is imparted to lever 82, despite the fact that knife assembly 180 is being advanced towards the extended position.

Figure 7:
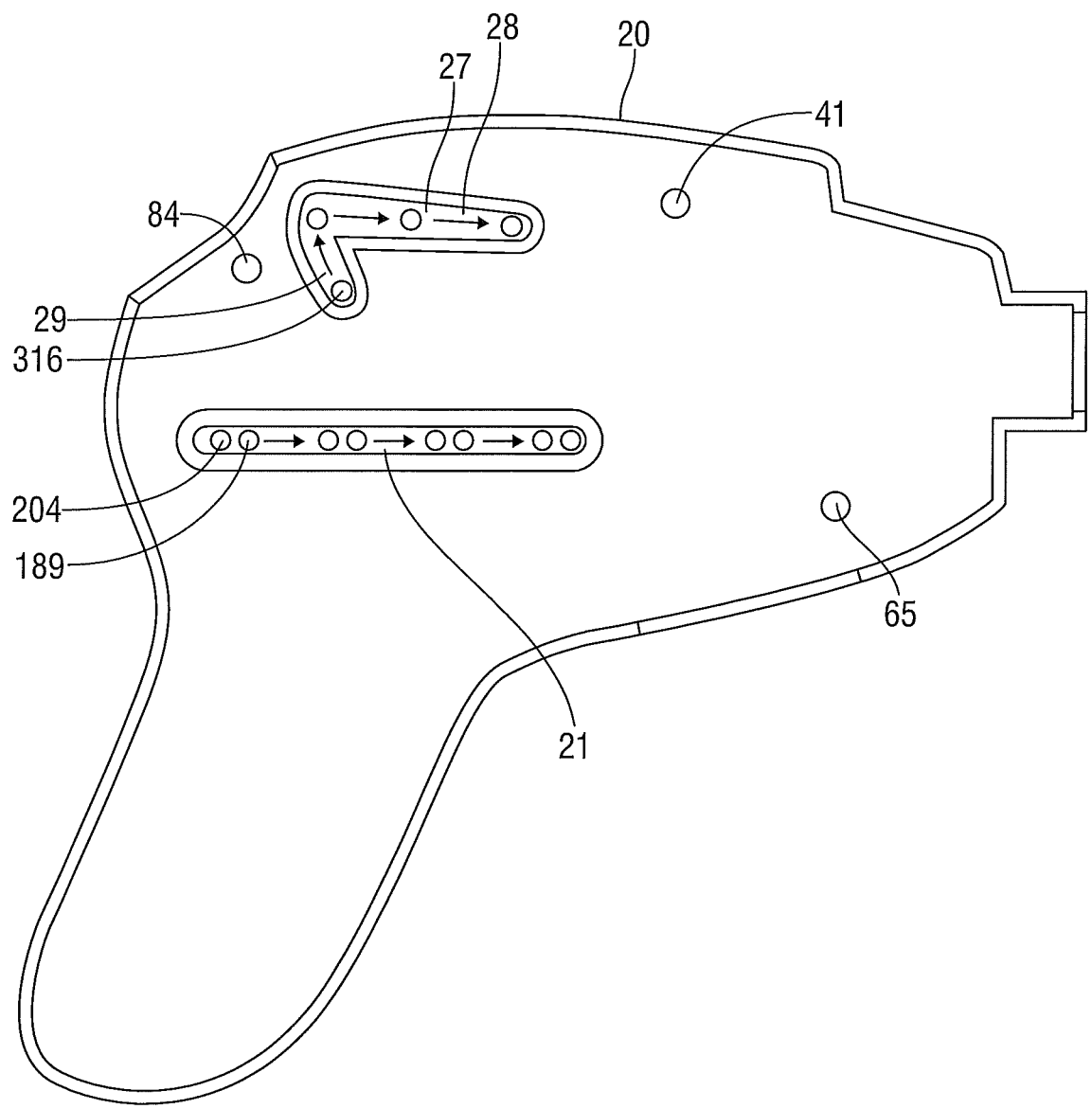
FIG. 7 is a side, interior view of a portion of the housing of the forceps of FIG. 1.
Figure 8D:
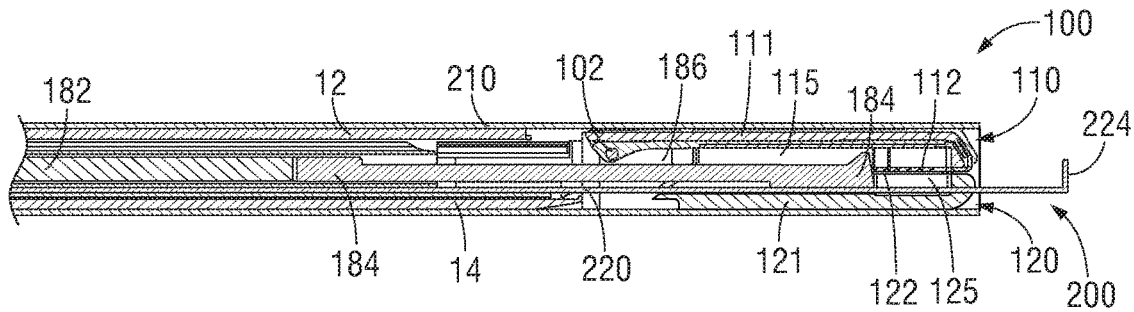
FIG. 8D is a longitudinal, cross-sectional view of the end effector assembly of FIG. 2 with the knife disposed in the extended position and the monopolar assembly disposed in a deployed position.

With reference to FIG. 7, in conjunction with FIGS. 4-6, as mentioned above, housing 20 includes a pair of longitudinal tracks 21 (only one is shown) defined on either side thereof, and a pair of linkage tracks 27 (only one is shown) defined on either side thereof. Each longitudinal track 21, as mentioned above, is configured to guide translation of lateral protrusions 189 of base member 188 of connector 68 and transverse pin 204 of hub 203 of drive shaft 202 therealong so as to guide translation of knife assembly 180 and monopolar assembly 200, respectively, along substantially longitudinal paths. The proximal and distal ends of longitudinal tracks 21 may also be configured to define the retracted and extended positions of knife 184 and/or the retracted and deployed positions of monopolar assembly 200, since translation of lateral protrusions 189 and transverse pin 204 through longitudinal tracks 21 is limited at least by the length of longitudinal tracks 21, e.g., the proximal and distal ends thereof.

Each linkage track 27 defined within housing 20 is configured to guide translation of first pin 316 of linkage members 310 through housing 20 and to provide a safety lockout feature that inhibits accidental actuation of monopolar assembly 200. More specifically, linkage tracks 27 each include a first, generally longitudinal portion 28 and a second portion 29 that angles downwardly and distally from the proximal end of first portion 28. Thus, as will be described in greater detail below, with first pin 316 disposed at the bases of second portions 29 of linkage tracks 27 and biased distally via biasing member 140, linkage members 310 are maintained in position and, thus, monopolar assembly 200 is locked in the retracted position. In this position, proximal end 144 of biasing member 140 is substantially fixed in position such that biasing member 140 may function to bias trigger assembly 60 towards the un-actuated position, thereby biasing knife 184 towards the retracted position. Once removed from second portions 29 of linkage tracks 27, first pin 316 is permitted to translate along first portions 28 of linkage tracks 27 such that the tension on biasing member 140 remains substantially unchanged during actuation of monopolar assembly 200, thereby substantially removing the biasing force of biasing member 140 from application during actuation of lever assembly 80.

Turning now to FIGS. 8A-8D, in conjunction with FIGS. 1-7, the use and operation of forceps 10 in both the bipolar mode, e.g., for grasping, treating and/or cutting tissue, and the monopolar mode, e.g., for electrical/electromechanical tissue treatment, is described. Initially, with respect to the bipolar mode, as shown in FIG. 8A, jaw members 110, 120 are disposed in the spaced-apart position. In the bipolar mode, monopolar assembly 200 remains disposed in the retracted position, as shown in FIGS. 8A-8C, wherein insulative sleeve 210 is positioned proximally of jaw members 110, 120 and energizable rod member 220 is disposed in the retracted position within insulative member 126 of jaw member 120. At this point, trigger assembly 60 is disposed in the un-actuated position such that knife 184 is disposed in the retracted position, lever 82 of lever assembly 80 is disposed at the proximal end 25 of recess 24 such that monopolar assembly 200 is disposed in the retracted position, and first pin 316 is disposed within second portions 29 of linkage tracks 27.

With jaw members 110, 120 disposed in the spaced-apart position, end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween, as shown in FIG. 8B. In this approximated position, energy may be supplied, e.g., via activation of switch 4, to plate 112 of jaw member 110 and/or plate 122 of jaw member 120 and conducted through tissue to treat tissue, e.g., to effect a tissue seal or otherwise treat tissue in the bipolar mode of operation.

Once tissue treatment is complete (or to cut untreated tissue), knife 184 of knife assembly 180 may be deployed from within shaft 12 to between jaw members 110, 120, e.g., via actuation of trigger 62 of trigger assembly 60, to cut tissue grasped therebetween. More specifically, upon actuation of trigger 62, knife 184 is advanced distally from shaft 12 to extend at least partially through knife channels 115, 125 of jaw members 110, 120, respectively, to cut tissue grasped between jaw members 110, 120 (FIG. 8C). Upon actuation of trigger 62, protrusions 189 of knife drive bar 182 are translated along longitudinal tracks 21 of housing 20 to guide translation of knife 184 to the extended position. Further, at this point, first pin 316 remains disposed within second portions 29 of linkage tracks 27. As such, proximal end 144 of biasing member 140 remains fixed in position while distal end 142 of biasing member 140 is advanced distally upon actuation of trigger 62. During actuation of trigger 62, first pin 316 is biased further towards the base of second portions 29 of linkage tracks 27 via biasing member 140, thus locking monopolar assembly 200 in position and inhibiting accidental deployment of monopolar assembly.

When tissue cutting is complete, trigger 62 may be released to allow connector 68 and knife drive rod 182 to return proximally under the bias of biasing member 142 such that knife 184 is returned to the retracted position within shaft 12. Next, jaw members 110, 120 may be moved back to the spaced-apart position (FIG. 8A) to release the treated and/or divided tissue.

For operation of forceps 10 in the monopolar mode, movable handle 40 is first depressed relative to fixed handle 50 to pivot jaw member 110 relative to jaw member 120 from the spaced-apart position to the approximated position. With jaw members 110, 120 disposed in the approximated position, monopolar assembly 200 may be translated from the retracted position (FIG. 8C) to the deployed position (FIG. 8D) via actuation of lever assembly 80. More specifically, in order to translate insulative sleeve 210 and energizable rod member 220 of monopolar assembly 200 from the retracted position (FIG. 8C) to the deployed position (FIG. 8D), lever 82 is rotated through recess 24 of housing 20 from the proximal end 25 thereof to the distal end 26 thereof. Rotation of lever 82 in this manner rotates arms 90 similarly to urge pin 204 of hub 203 of drive shaft 202 distally such that insulative sleeve 210 is translated distally to the deployed position, wherein insulative sleeve 210 surrounds jaw members 110, 120 (FIG. 8D) and energizable rod member 220 is likewise translated distally to the deployed position, wherein energizable rod member 220 extends distally from end effector assembly 100 (FIG. 8D).

At the same time as monopolar assembly 200 is advanced distally, arms 90 urge connector 68 distally such that pin 69 is advanced distally and such that knife 184 is translated from the extended position towards the retracted position. However, rotation of arms 90 also effects distal advancement of linkage members 310, as first pin 316 is moved along linkage slots 27 from the second portion 29 thereof to the first portion 28 thereof. Once first pin 316 reaches first portion 28 of linkage slots 27 and is thus permitted to translate distally therealong, linkage members 310 are permitted to move distally to urge proximal end 144 of biasing member 140 distally a substantially equal distance as the distal translation of distal end 142 of biasing member 140, which is engaged to pin 69. As such, with a reduced (or removed) tension on biasing member 140, a reduced biasing force (or no biasing force) from biasing member 140 is felt upon actuation of lever 82.

Once monopolar assembly 200 is disposed in the deployed position, activation switch 4 may be actuated to supply energy to energizable rod member 220 to treat, e.g., dissect, tissue. During application of energy to tissue via energizable rod member 220, forceps 10 may be moved relative to tissue, e.g., longitudinally along longitudinal axis "X-X" and/or radially therefrom, to facilitate electromechanical treatment of tissue. At the completion of tissue treatment, e.g., dissection, monopolar assembly 200 may be returned to the retracted position (FIG. 8C) via rotating lever 82 from the distal end 26 of recess 24 back to the proximal end 25 thereof. Rotation of lever 82 from the second position back to the first position rotates arms 90 back to their initial position such that linkage members 310, trigger assembly 60, and knife assembly 180 are likewise returned to their respective initial positions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a first actuation assembly coupled to a first component and selectively movable from a first position to a second position to move the first component distally from a first proximal position towards a first distal position;
   a biasing member having a distal end portion coupled directly to the first actuation assembly and configured to apply a biasing force to the first actuation assembly to bias the first component proximally towards the first proximal position;
   a second actuation assembly coupled to a second component and selectively actuatable to move the second component distally from a second proximal position towards a second distal position, the second actuation assembly coupled to the first actuation assembly such that actuation of the second actuation assembly effects movement of the first component from the first proximal position towards the first distal position; and
   a linkage assembly coupled to the second actuation assembly and directly coupled to a proximal end portion of the biasing member, the linkage assembly configured to reduce the biasing force applied to the first component when the second actuation assembly effects movement of the first component from the first position towards the first distal position.

2. The surgical instrument according to claim 1, wherein at least a portion of the second actuation assembly is configured to contact at least a portion of the first actuation assembly upon actuation of the second actuation assembly to urge the first actuation assembly from the first position towards the second position.

3. The surgical instrument according to claim 1, wherein the first actuation assembly includes a trigger pivotably coupled thereto and selectively movable from an unactuated position to an actuated position for moving the first actuation assembly from the first position to the second position.

4. The surgical instrument according to claim 1, wherein the second actuation assembly includes a lever pivotable from a proximal position to a distal position for actuating the second actuation assembly.

5. The surgical instrument according to claim 1, wherein the first and second actuation assemblies are at least partially disposed within a housing.

6. The surgical instrument according to claim 5, wherein the housing defines at least one track configured to guide movement of at least one of the first actuation assembly between the first and second positions and actuation of the second actuation assembly.

7. The surgical instrument according to claim 1, wherein the first actuation assembly is configured to move the first distal end of the biasing member distally upon movement of the first actuation assembly from the first position towards the second position.

8. The surgical instrument according to claim 7, wherein the linkage assembly is configured to maintain the proximal end of the biasing member in substantially fixed position when the second actuation assembly is un-actuated.

9. The surgical instrument according to claim 7, wherein the linkage assembly is configured to move the proximal end of the biasing member distally upon actuation of the second actuation assembly.

10. The surgical instrument according to claim 9, wherein the linkage assembly is configured to move the proximal end of the biasing member distally a distance that is substantially equal to a distance the first actuation assembly is configured to move the distal of the biasing member distally upon movement of the first actuation assembly from the first position towards the second position.

11. A method of actuating components of a surgical instrument, comprising:
    moving a first actuation assembly from a first position to a second position to move a first component distally against a biasing force from a first proximal position towards a first distal position;
    returning the first actuation assembly from the second position back to the first position such that the first component is returned proximally back to the first proximal position; and
    moving a second actuation assembly to move a second component distally from a second proximal position towards a second distal position, wherein moving the second actuation assembly effects movement of the first component from the first proximal position towards the first distal position against a reduced biasing force, the second actuation assembly coupled to a linkage assembly, the linkage assembly directly connected to a proximal end portion of a biasing member, and a distal end portion of the biasing member coupled directly to the first actuation assembly to generate the reduced biasing force applied to the first component.

12. The method according to claim 11, wherein a trigger is moved from an un-actuated position to an actuated position to move the first actuation assembly from the first position to the second position.

13. The method according to claim 11, wherein a lever is moved from a proximal position to a distal position to move the second actuation assembly.

14. The method according to claim 11, wherein the biasing member applies the biasing force to bias the first actuation assembly towards the first position, thereby biasing the first component towards the first proximal position.

15. The method according to claim 11, wherein the first actuation assembly is returned from the second position to the first position under the biasing force, thereby returning the first component to the first proximal position under the biasing force.

* * * * *